(12) United States Patent
Suzuki

(10) Patent No.: US 8,916,839 B2
(45) Date of Patent: Dec. 23, 2014

(54) SAMPLE PREPARATION METHOD AND APPARATUS

(71) Applicant: Hitachi High-Tech Science Corporation, Tokyo (JP)

(72) Inventor: Hidekazu Suzuki, Tokyo (JP)

(73) Assignee: Hitachi High-Tech Science Corporation (JP)

( * ) Notice: Subject to any disclaimer, the term of this patent is extended or adjusted under 35 U.S.C. 154(b) by 0 days.

(21) Appl. No.: 13/771,386

(22) Filed: Feb. 20, 2013

(65) Prior Publication Data

US 2013/0214458 A1    Aug. 22, 2013

(30) Foreign Application Priority Data

Feb. 21, 2012    (JP) .................................. 2012-035391

(51) Int. Cl.
  *G21K 5/04*    (2006.01)
  *H01J 37/26*    (2006.01)
  *H01J 37/305*    (2006.01)
  *G01N 1/32*    (2006.01)

(52) U.S. Cl.
  CPC .............. *H01J 37/3053* (2013.01); *G01N 1/32* (2013.01); *H01J 2237/30455* (2013.01); *H01J 2237/30488* (2013.01); *H01J 2237/31745* (2013.01)
  USPC ..................... 250/492.3; 250/492.1; 250/307; 250/310

(58) Field of Classification Search
  USPC .............. 250/305, 306, 307, 310, 311, 492.1, 250/492.3
  See application file for complete search history.

(56) References Cited

U.S. PATENT DOCUMENTS

| | | | |
|---|---|---|---|
| 7,482,586 B2 * | 1/2009 | Ishitani et al. | 250/306 |
| 7,915,581 B2 * | 3/2011 | Ishitani et al. | 250/307 |
| 2004/0245464 A1 * | 12/2004 | Iwasaki et al. | 250/307 |
| 2005/0184251 A1 * | 8/2005 | Oi et al. | 250/492.3 |
| 2008/0185517 A1 * | 8/2008 | Frosien | 250/289 |
| 2008/0296497 A1 * | 12/2008 | Tomimatsu et al. | 250/309 |
| 2010/0008563 A1 | 1/2010 | Fujii et al. | 382/149 |

FOREIGN PATENT DOCUMENTS

JP    2009204480    9/2009

* cited by examiner

*Primary Examiner* — Nicole Ippolito
(74) *Attorney, Agent, or Firm* — Adams & Wilks

(57) ABSTRACT

A sample preparation method is carried out using a focused ion beam and an electron beam. While displaying a SEM image of a first cross-section of a sample on a display screen, the first cross-section is subjected to etching processing by scanning and irradiation of the focused ion beam, thereby exposing a second cross-section, and while displaying a SEM image of the second cross-section on the display screen, the scanning direction of the focused ion beam is changed while performing scanning and irradiation of the focused ion beam and subjecting the second cross-section to etching processing, thereby exposing a desired cross-section of the sample.

7 Claims, 6 Drawing Sheets

SAMPLE PREPARATION METHOD AND APPARATUS

This application claims priority from Japanese Patent Application No. 2012-035391 filed on Feb. 21, 2012, the entire subject-matter of which is incorporated herein by reference.

BACKGROUND OF THE INVENTION

1. Field of the Invention

The present invention relates to a sample preparation method and apparatus for preparing a sample by etching processing using a focused ion beam.

2. Description of the Related Art

As a method of analyzing internal structure and defects in a semiconductor device or the like, there is known a cross-section processing and observation method, in which a focused ion beam is used for cross-section processing of a sample to expose a cross-section including a desired structure or a defect and a scanning electron microscope is used to observe the cross-section. According to this method, a desired observation target inside the sample can be exposed with pinpoint accuracy, and hence the structure or the defect can be observed quickly.

As a method for exposing a desired observation target, there is disclosed a method of repeatedly performing cross-section processing and cross-section observation, and finishing the cross-section processing at the timing when an observation target appears in a cross-sectional observation image (see JP-A-2009-204480). According to this method, a cross-section including a desired observation target can be exposed accurately.

As another analysis method, there is also known a method of preparing a sample piece including a desired observation target from a sample by a focused ion beam and observing the sample piece by a transmission electron microscope. According to this method, an observation target can be observed by the transmission electron microscope with a high resolution.

In the case of using a focused ion beam to expose a cross-section of a semiconductor device or prepare a sample piece, it is important to process a cross-section along an arrangement direction of a device pattern in a semiconductor wafer.

In the cross-section processing and observation method, the structure or defects are observed from an observation image of a cross-section including a device pattern, and hence it is necessary to expose the cross-section along the arrangement direction of the device pattern. Further, in the preparation of the sample piece, the internal structure of the sample piece is analyzed by transmission electron microscope (TEM) observation, and hence it is necessary to prepare a sample piece which has a desired structure inside, and is along the arrangement direction of the device pattern.

However, in recent years, the device pattern has become finer along with densification and reduction in size of semiconductor devices. Thus, it has been difficult for the conventional method to check the arrangement direction of the device pattern by observation and form the cross-section along the arrangement direction of the device pattern.

SUMMARY OF THE INVENTION

Illustrative aspects of the present invention provide a sample preparation method and apparatus for preparing a sample along an arrangement direction of a fine device pattern.

(1) According to one illustrative aspect of the present invention, there is provided a sample preparation method, including: while displaying an observation image of a cross-section, which is a first cross-section, of a sample under scanning electron microscope observation on a display screen, subjecting the first cross-section to etching processing by scanning and irradiation of a focused ion beam, thereby exposing a second cross-section of the sample; and while displaying an observation image of the second cross-section under scanning electron microscope observation on the display screen, changing a scanning direction of the focused ion beam while performing the scanning and irradiation of the focused ion beam and subjecting the second cross-section to the etching processing by the scanning and irradiation of the focused ion beam having the changed scanning direction, thereby exposing a desired cross-section of the sample.

With this configuration, a cross-section along an arrangement direction of an internal device pattern of the sample can be exposed. The scanning direction of the focused ion beam can be adjusted while observing the sample by a scanning electron microscope in real time. Thus, even in a case of a device pattern in which devices are arranged at an interval of the order of several tens of nanometers, the formation direction of the cross-section and the arrangement direction of the device pattern can be aligned with each other accurately.

(2) According to another illustrative aspect of the present invention, there is provided a sample preparation apparatus, including: a sample stage configured to place a sample thereon; a focused ion beam column configured to scan and irradiate the sample with a focused ion beam for exposing a cross-section of the sample; an electron beam column configured to scan and irradiate the cross-section with an electron beam; a charged particle detector configured to detect a charged particle emitted from the cross-section by irradiation of the electron beam; a display portion configured to display an observation image of the cross-section formed by a detection signal of the charged particle detector; an input portion configured to receive an input of a rotation angle of a scanning direction of the focused ion beam; and a scanning direction control portion configured to change the scanning direction of the focused ion beam during processing and observation of the cross-section, based on the rotation angle input via the input portion.

With this configuration, the scanning direction of the focused ion beam can be adjusted while looking at an observation image of the cross-section under processing, which is displayed on the display portion.

According to the sample preparation apparatus and method of the present invention, even in the case of a sample having a fine device pattern, the cross-section along the arrangement direction of the device pattern can be formed, and hence a sample for analyzing the fine internal structure or defects can be prepared.

DETAILED DESCRIPTION

A sample preparation apparatus and method according to an embodiment of the present invention will be described below.

Figure 1:
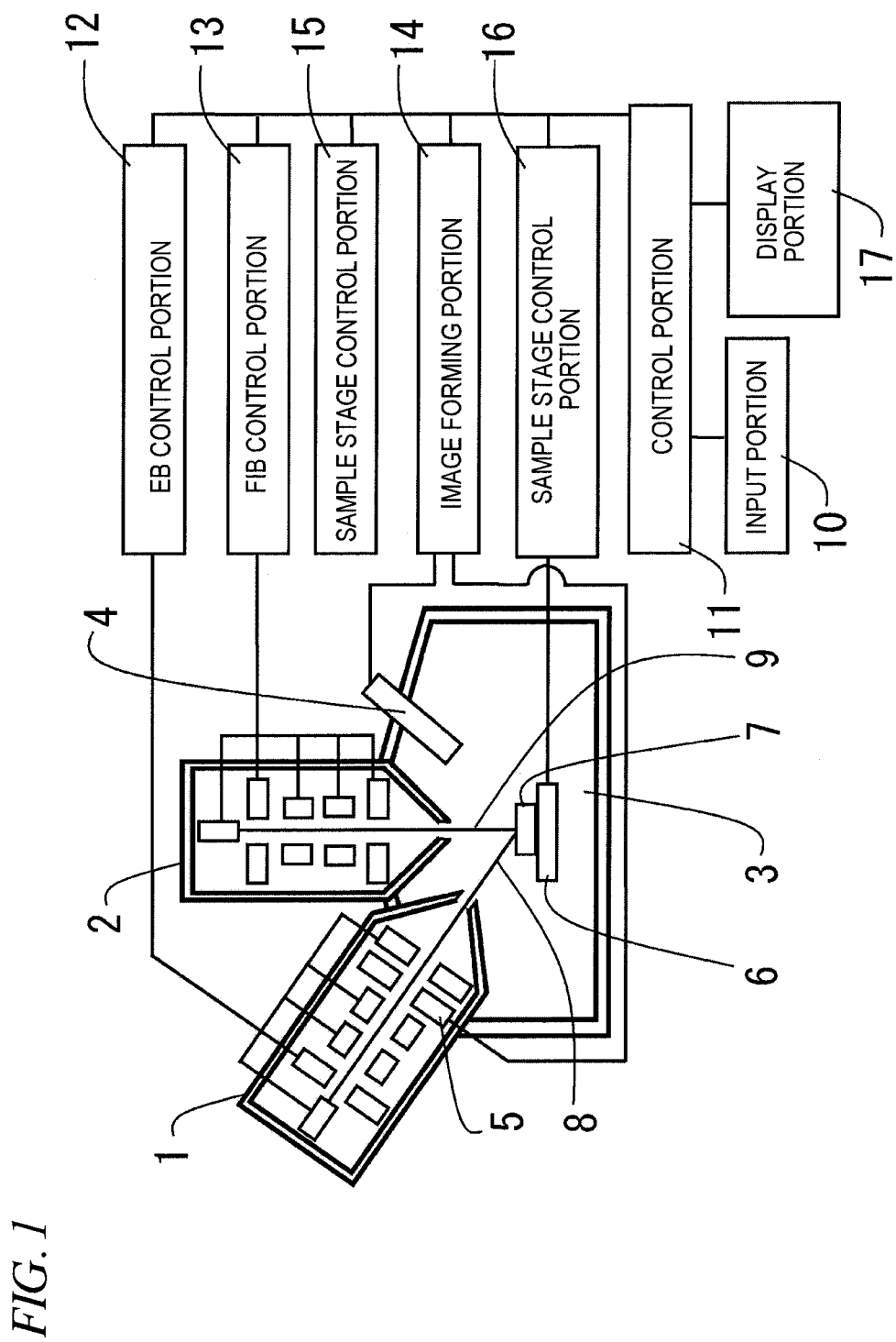
FIG. 1 is a configuration diagram of a sample preparation apparatus according to an embodiment of the present invention.

As illustrated in FIG. 1, the sample preparation apparatus in this embodiment includes an EB column 1, a FIB column 2, and a sample chamber 3. The EB column 1 and the FIB column 2 irradiate a sample 7 accommodated in the sample chamber 3 with an electron beam 8 and an ion beam 9, respectively.

The sample preparation apparatus further includes a secondary electron detector 4 and a backscattered electron detector 5 as charged particle detectors. The secondary electron detector 4 is capable of detecting secondary electrons generated from the sample 7 by irradiation of the electron beam 8 or the ion beam 9. The backscattered electron detector 5 is provided inside the EB column 1. The backscattered electron detector 5 is capable of detecting backscattered electrons reflected by the sample 7 as a result of the irradiation of the electron beam 8 to the sample 7.

The sample preparation apparatus further includes a sample stage 6 for placing the sample 7 thereon. The sample stage 6 can be tilted to change an incident angle of the ion beam 9 to the sample 7. The tilt of the sample stage 6 is controlled by a sample stage control portion 16.

The sample preparation apparatus further includes an EB control portion 12, a FIB control portion 13, an image forming portion 14, and a display portion 17. The EB control portion 12 transmits an irradiation signal to the EB column 1 to control the EB column 1 to radiate the electron beam 8. The FIB control portion 13 transmits an irradiation signal to the FIB column 2 to control the FIB column 2 to radiate the ion beam 9. The image forming portion 14 forms a backscattered electron image based on a signal for scanning the electron beam 8 sent from the EB control portion 12 and a signal of the backscattered electrons detected by the backscattered electron detector 5. The display portion 17 is capable of displaying the backscattered electron image. The image forming portion 14 forms data of a SEM image based on the signal for scanning the electron beam 8 sent from the EB control portion 12 and a signal of the secondary electrons detected by the secondary electron detector 4. The display portion 17 is capable of displaying the SEM image. Further, the image forming portion 14 forms data of a SIM image based on a signal for scanning the ion beam 9 sent from the FIB control portion 13 and a signal of the secondary electrons detected by the secondary electron detector 4. The display portion 17 is capable of displaying the SIM image.

The sample preparation apparatus further includes an input portion 10 and a control portion 11. An operator inputs conditions on the apparatus control, such as a beam irradiation condition, to the input portion 10. The input portion 10 transmits the input information to the control portion 11. The control portion 11 transmits a control signal to the EB control portion 12, the FIB control portion 13, the image forming portion 14, the sample stage control portion 16, or the display portion 17, to thereby control the operation of the sample preparation apparatus.

Description is given of the control of the apparatus. For example, the operator sets an irradiation region of the ion beam 9 based on an observation image displayed on the display portion 17, such as the backscattered electron image, the SEM image, or the SIM image. The operator inputs, via the input portion 10, a processing frame for setting the irradiation region on the observation image displayed on the display portion 17. The processing frame as used herein is a frame indicating a boundary between a region to be irradiated with the ion beam 9 and a region not to be irradiated with the ion beam 9. When the operator inputs an instruction to start processing to the input portion 10, a signal indicating the irradiation region and a signal indicating the start of processing are transmitted from the control portion 11 to the FIB control portion 13, and the FIB control portion 13 radiates the ion beam 9 to the specified irradiation region of the sample 7. In this manner, the irradiation region input by the operator can be irradiated with the ion beam 9.

A scanning direction control portion 15 generates, based on a scanning direction of the ion beam 9 input to the input portion 10, a signal for changing the scanning direction of the ion beam 9, and transmits the signal to the FIB control portion 13. The FIB control portion 13 transmits a control signal to the FIB column 2 to change the scanning direction of the ion beam 9 to be radiated from the FIB column 2. Incidentally, the scanning direction control portion 15 is capable of changing the scanning direction of the ion beam 9 even under the state where the sample 7 is scanned and irradiated with the electron beam 8 and the ion beam 9 from the EB column 1 and the FIB column 2, respectively.

First Example

Referring to FIGS. 2A to 4, description is given of a sample preparation method according to this example, which relates to cross-section processing and observation for analysis of internal structure of a sample having a device pattern.

Figure 2A:
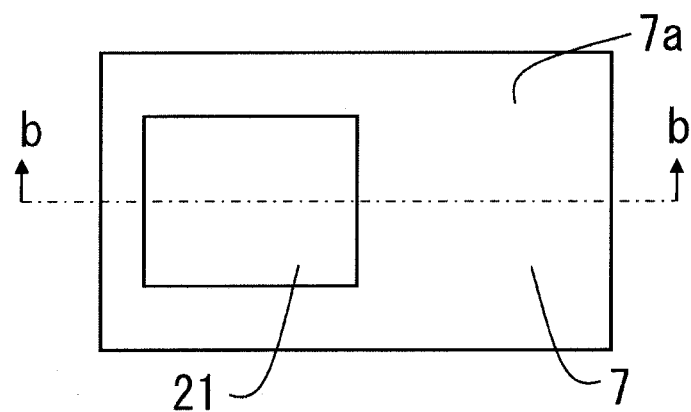
FIGS. 2A and 2B are explanatory diagrams of a sample surface and a sample cross-section, respectively, according to a first example of the present invention.
Figure 2B:
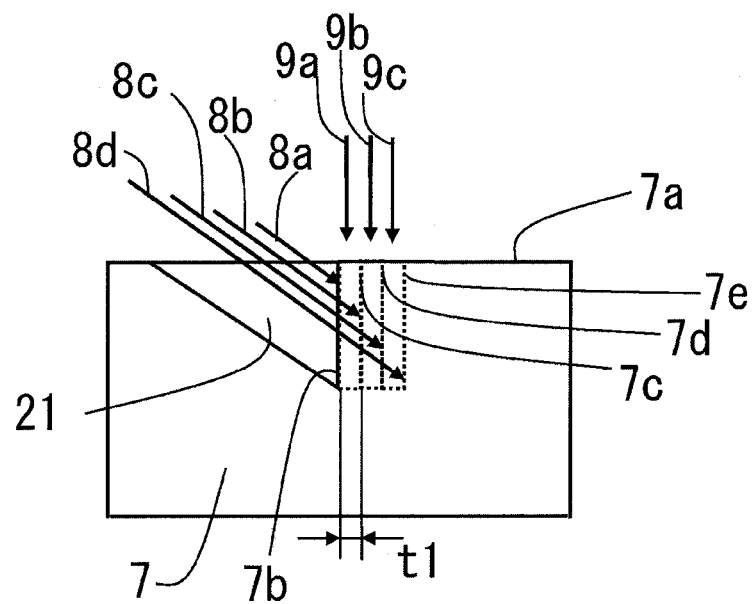

FIG. 2A is a diagram of the sample 7 as viewed from a surface 7a side. First, the sample 7 is scanned and irradiated with the ion beam 9 from the surface 7a side to form a processing groove 21 in part of the surface 7a. FIG. 2B is a diagram taken along the cross-section b-b of FIG. 2A. In order to observe a cross-section 7b exposed by preparation of the processing groove 21, the cross-section 7b is scanned and irradiated with an electron beam 8a. In this manner, a SEM image of the cross-section 7b is displayed on the display portion 17.

In order to expose a defect present inside the sample 7, cross-section processing by the ion beam 9 is performed. In this case, in order to check the defect, the cross-sections under the cross-section processing are continuously observed by a scanning electron microscope. In other words, during processing for exposing cross-sections 7c, 7d, and 7e by ion beams 9a, 9b, and 9c, respectively, the cross-sections 7c, 7d, and 7e are irradiated with electron beams 8b, 8c, and 8d to display respective SEM images of the cross-sections 7c, 7d, and 7e in real time. SEM images in the course of exposing the cross-sections are also displayed in real time.

In this case, an interval t1 between the cross-section 7b and the cross-section 7c formed by the ion beam 9a is equal to an interval between the cross-section 7c and the cross-section 7d formed by the ion beam 9b and an interval between the cross-section 7d and the cross-section 7e formed by the ion beam 9c. In this example, the interval t1 is set to 1 nm, and, after the ion beam 9 is scanned once in the scanning direction, the ion beam 9 is moved by 1 nm in a sub-scanning direction perpendicular to the scanning direction of the ion beam 9, and then the ion beam 9 is scanned once again in the scanning direction. In this manner, the scanning of the ion beam 9 in the scanning direction and the movement of the ion beam 9 in the sub-scanning direction are repeatedly performed.

As described above, the cross-sections during processing are observed in real time, and hence the cross-section processing can be finished when a defect as an observation target appears in a SEM image, and the defect can be analyzed by observing the cross-section including the defect.

Incidentally, in the case of analysis of the structure of a sample having a device pattern, it is necessary to expose a cross-section along the arrangement direction of the device pattern. This is because the device structure can be analyzed only through an observation image of a cross-section in which the original shape of the device pattern appears.

Figure 3A:
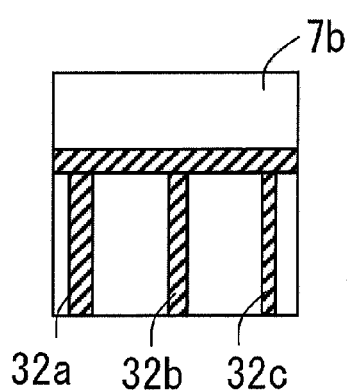
FIGS. 3A to 3D are explanatory diagrams of a processing method according to the first example of the present invention.
Figure 3B:
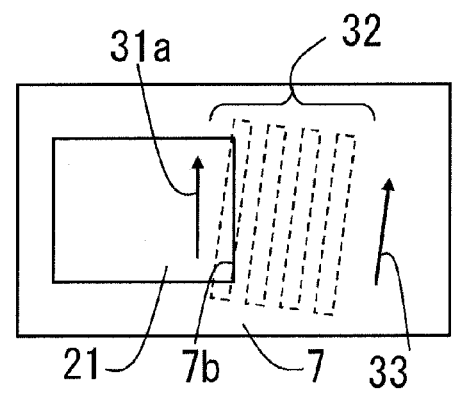

FIG. 3B is a diagram of the sample 7 as viewed from the surface thereof. In the case where an arrangement direction 33 of a device pattern 32 is not parallel to a scanning direction 31a of the ion beam 9 for exposing the cross-section 7b by irradiation, as illustrated in a SEM image of the cross-section 7b of FIG. 3A, device structures 32a, 32b, and 32c are exposed in the cross-section 7b as structures having different widths. If the device structures are analyzed from the SEM image of the cross-section 7b, the device structures 32a, 32b, and 32c are erroneously determined to be the device structures having different widths.

Figure 3C:
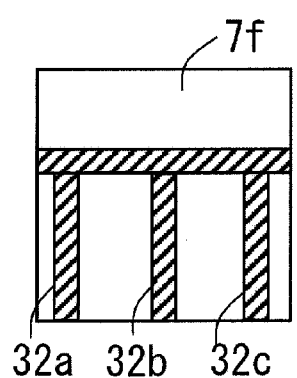
Figure 3D:
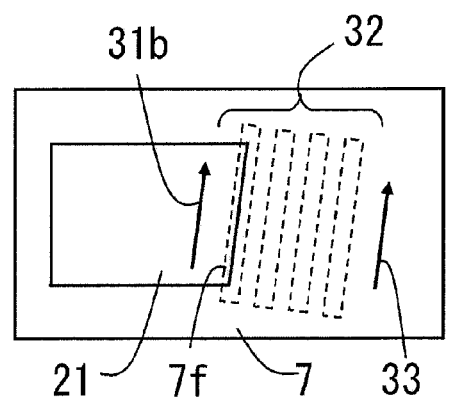

To deal with this problem, the scanning direction 31a of the ion beam 9 is rotated in the plane of the surface 7a of the sample 7 so that the scanning direction 31a may be parallel to the arrangement direction 33 of the device pattern 32. As illustrated in FIG. 3D, the scanning direction 31b of the ion beam 9 is rotated so as to be parallel to the arrangement direction 33 of the device pattern 32, and the sample 7 is processed by the ion beam 9 to expose a cross-section 7f. FIG. 3C is a SEM image of the cross-section 7f. This SEM image reflects the original device structures of the device pattern 32, in which the device structures 32a, 32b, and 32c having the same width are displayed. In this manner, accurate structural analysis can be performed from the SEM image of the cross-section.

Now, description is given of a method of changing the scanning direction of the ion beam 9.

Figure 4:
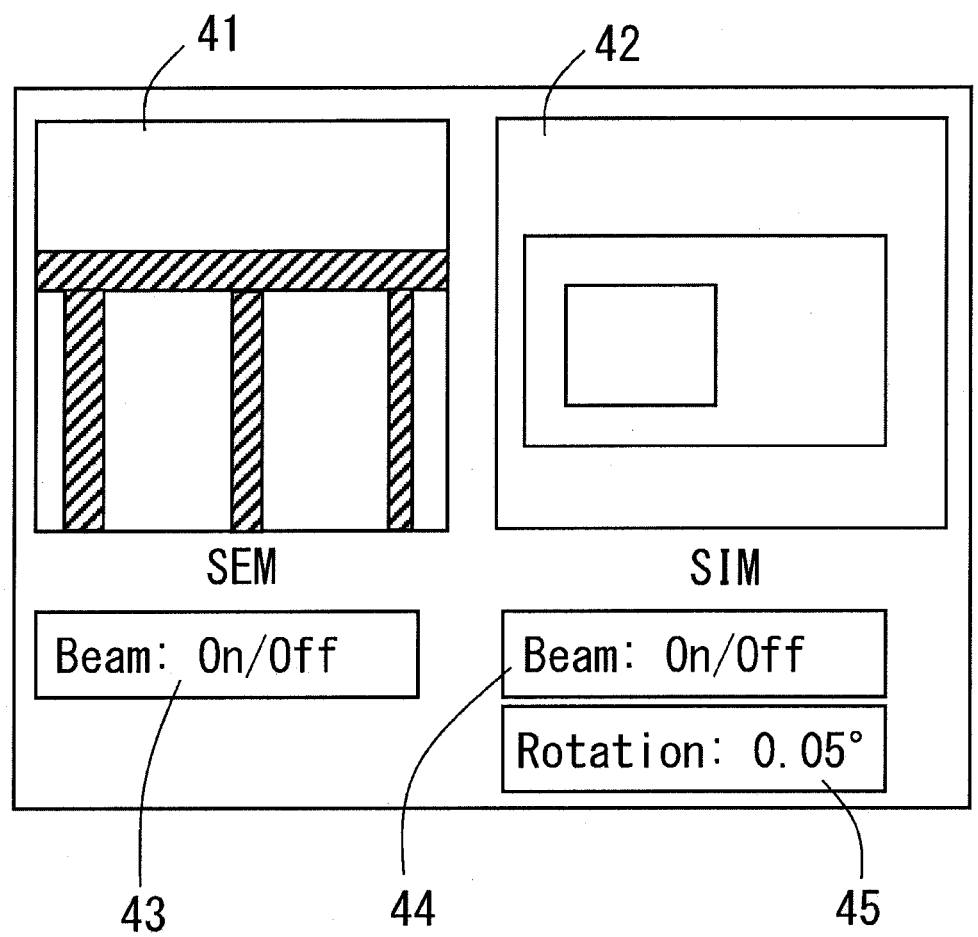
FIG. 4 is a configuration diagram of a display screen according to the first example of the present invention.

FIG. 4 is a configuration diagram of a display screen of the display portion 17. The sample preparation apparatus in this example is capable of scanning and radiating the electron beam 8 and the ion beam 9 independently, and controlling the irradiation start and stop of the respective beams by operations of an electron beam irradiation button 43 and an ion beam irradiation button 44 via the input portion 10. In the case where the sample 7 is irradiated with both the electron beam 8 and the ion beam 9, respective observation images of an SEM image 41 and a SIM image 42 can be displayed on the display screen in real time.

When a rotation angle of the ion beam 9 is input via the input portion 10, the rotation angle is displayed in a rotation angle display section 45 of the display screen. Based on the rotation angle, the scanning direction control portion 15 rotates the scanning direction of the ion beam 9. The rotation angle as used herein refers to a rotation angle in the plane of the surface 7a of the sample 7 with respect to the scanning direction as a reference. In this example, the rotation angle is input in increments of 0.01 degrees to change the scanning direction.

The scanning direction control portion 15 is capable of rotating the scanning direction during the scanning and irradiation of the ion beam 9. In this manner, it is unnecessary to suspend the processing by the ion beam 9 for the rotation adjustment of the scanning direction, resulting in the function and effect that the cross-section processing can be performed efficiently.

The scanning direction control portion 15 is also capable of rotating the scanning direction of the ion beam 9 during scanning electron microscope observation. In this manner, the scanning direction of the ion beam 9 can be adjusted while observing the cross-section under processing, and hence even the fine adjustment of the rotation angle can be performed accurately. In addition, the scanning direction can be rotated without stopping the scanning and irradiation of the ion beam 9 and without stopping the scanning electron microscope observation, and hence a time period necessary for the cross-section processing can be shortened significantly.

Further, the cross-section that reflects the original shape of the device pattern can be exposed, and hence this example provides the remarkable function and effect also in the case of analysis of the device pattern structure.

Although the SEM image is used in the description in the above-mentioned example, a backscattered electron image can be used instead of the SEM image.

Second Example

Referring to FIGS. 5A to 5C and FIG. 6, description is given of a sample preparation method according to this example, which relates to a sample for TEM observation.

Figure 5A:
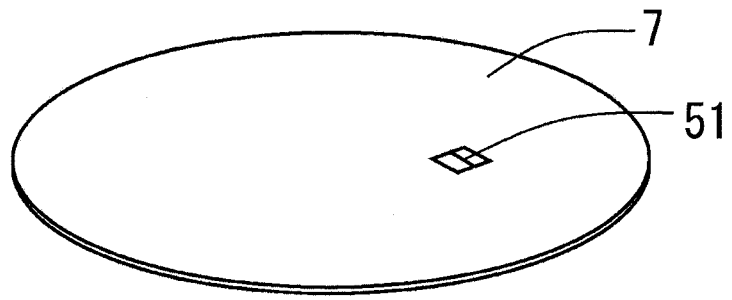
FIGS. 5A to 5C are explanatory diagrams of preparation of a sample for TEM observation according to a second example of the present invention.
Figure 5B:
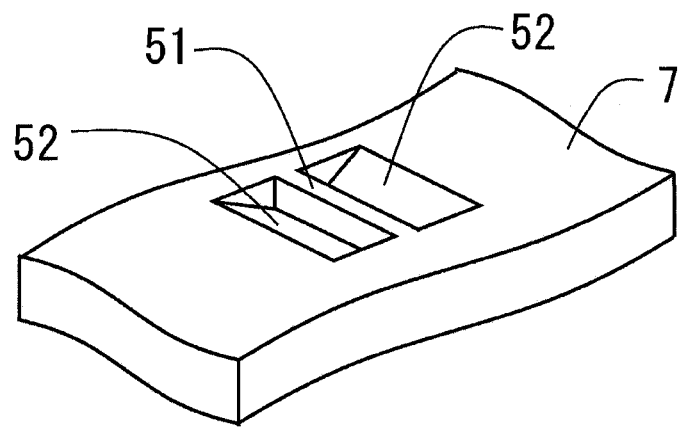
Figure 5C:
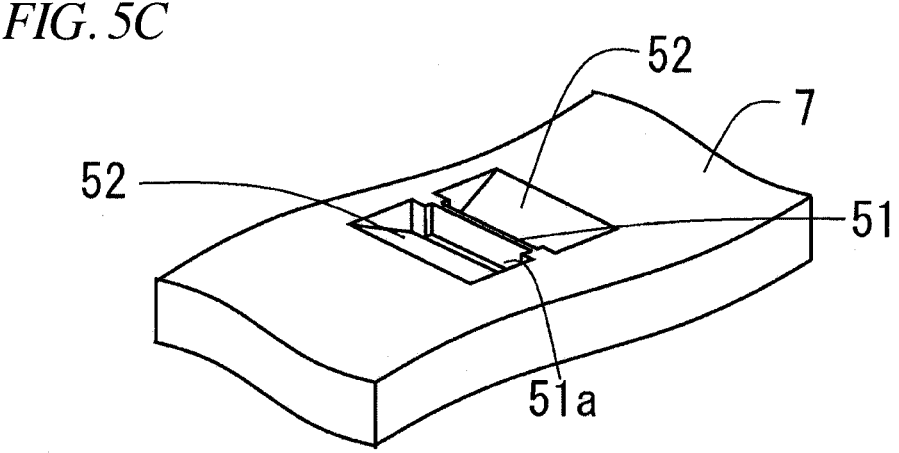

FIG. 5A is a diagram of a sample 7 as a semiconductor wafer. In order to prepare a sample for TEM observation, processing for cutting out a lamellar sample 51 as a part of the sample 7 from the sample 7 is performed by the ion beam 9. FIG. 5B is an enlarged diagram of the lamellar sample 51 and its vicinity. Processing grooves 52 are formed on both sides of the lamellar sample 51 by the ion beam 9. Then, as illustrated in FIG. 5C, thinning processing is further performed so that the lamellar sample 51 may have a desired thickness, to thereby prepare the lamellar sample 51 for TEM observation.

Figure 6:
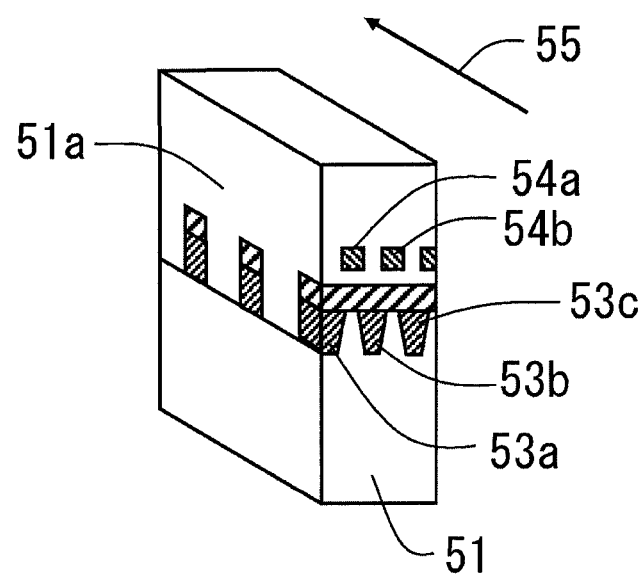
FIG. 6 is an explanatory diagram of the sample for TEM observation according to the second example of the present invention.

FIG. 6 is an explanatory diagram of the lamellar sample 51 for TEM observation. The lamellar sample 51 has the structure in which devices 54a and 54b are periodically arranged. The devices 54a and 54b are partitioned by element isolation (STI) regions 53a, 53b, and 53c provided for isolating the devices, and are placed in regions sandwiched by the element isolation (STI) regions.

In the thinning processing, the lamellar sample 51 is processed so that a desired device structure may be left inside the lamellar sample 51. For example, in the case of preparing a lamellar sample having only one device, the lamellar sample 51 is subjected to etching processing by the ion beam 9 so that only the element isolation (STI) region 53b, the element isolation (STI) region 53c and the device 54b, which is sandwiched by the element isolation (STI) region 53b and the element isolation (STI) region 53c, may be left. The interval between the devices is on the order of several tens of nanometers, and hence the final thickness of the lamellar sample 51 having only one device is extremely small. In a thinning processing method for preparing such a lamellar sample, it is important to scan and irradiate the sample with the ion beam 9 along the arrangement direction of the device pattern.

In the thinning processing method, the method described in the first example is used to rotate the scanning direction of the ion beam 9 so as to be parallel to an arrangement direction 55 of the device pattern. In other words, under the state where a cross-section 51a is scanned and irradiated with the electron beam 8 to perform scanning electron microscope observation, etching processing is performed by the ion beam 9 so as to reduce the thickness of the lamellar sample 51. While looking at a SEM image of the cross-section 51a by the scanning electron microscope observation under the etching processing, the scanning direction of the ion beam 9 is rotated so that the widths of the plurality of element isolation (STI) regions 53a exposed in the cross-section 51a may be uniform. In addition, similar etching processing is performed also on a cross-section on the opposite side of the cross-section 51a of the lamellar sample 51. Then, the internal device structure of the lamellar sample 51 is estimated based on the device pattern exposed in the cross-section and the thickness of the lamellar sample 51. The processing by the ion beam 9 is finished when only the element isolation (STI) region 53b, the element isolation (STI) region 53c and the device 54b, which is sandwiched by the element isolation (STI) region 53b and the element isolation (STI) region 53c, are left in the lamellar sample 51. In this manner, a desired lamellar sample 51 can be prepared.

According to the above-mentioned thinning processing method, even in the case of a sample for TEM observation having an extremely fine device pattern, the scanning direction of the ion beam 9 can be rotated while observing the sample by scanning electron microscope observation in real time. Thus, a desired lamellar sample can be prepared accurately. Further, the scanning direction of the ion beam 9 can be rotated without suspending the scanning and irradiation of the ion beam 9, and hence a desired lamellar sample can be prepared in a short period of time.

What is claimed is:

1. A sample preparation method, comprising:
    while displaying an observation image of a, first cross-section of a sample under scanning electron microscope observation on a display screen, subjecting the first cross-section to etching processing by scanning and irradiation of a focused ion beam, thereby exposing a second cross-section of the sample; and
    while displaying an observation image of the second cross-section under scanning electron microscope observation on the display screen, changing a scanning direction of the focused ion beam while performing the scanning and irradiation of the focused ion beam and subjecting the second cross-section to the etching processing by the scanning and irradiation of the focused ion beam having the changed scanning direction, thereby exposing a desired cross-section of the sample.

2. The sample preparation method according to claim 1, wherein the changing a scanning direction of the focused ion beam comprises changing the scanning direction so as to be parallel to an arrangement direction of a device pattern of the sample.

3. A sample preparation method for preparing a lamellar sample having the desired cross-section formed by the sample preparation method according to claim 1.

4. A sample preparation apparatus, comprising:
    a sample stage configured to place a sample thereon;
    a focused ion beam column configured to scan and irradiate the sample with a focused ion beam for exposing a cross-section of the sample;
    an electron beam column configured to scan and irradiate the cross-section with an electron beam;
    a charged particle detector configured to detect a charged particles emitted from the cross-section by irradiation of the electron beam;
    a display portion configured to display an observation image of the cross-section formed by a detection signal of the charged particle detector;
    an input portion configured to receive an input of a rotation angle of a scanning direction of the focused ion beam; and
    a scanning direction control portion configured to change the scanning direction of the focused ion beam during processing and observation of the cross-section based on the rotation angle received by the input portion.

5. The sample preparation apparatus according to claim 4, wherein the display portion is configured to display:
    one of a SEM image and a backscattered electron microscope image of the cross-section;
    a SIM image of the sample;
    a focused-ion-beam display section for instructing irradiation start and stop of the focused ion beam;
    an electron-beam display section for instructing irradiation start and stop of the electron beam; and
    a rotation angle display section for inputting the rotation angle.

6. The sample preparation apparatus according to claim 4, wherein the charged particle detector comprises one of a backscattered electron detector and a secondary electron detector.

7. The sample preparation apparatus according to claim 4, wherein the scanning direction control portion is configured to rotate the scanning direction of the focused ion beam while the focused ion beam column continuously scans and irradiates the sample with the focused ion beam.

* * * * *